United States Patent [19]
Knuth et al.

[11] Patent Number: 5,891,504
[45] Date of Patent: Apr. 6, 1999

[54] FLAVOR COMPOSITION

[75] Inventors: Mark E. Knuth, San Carlos; Om P. Sahai, San Mateo, both of Calif.

[73] Assignee: Samyang Genex Research Institute, Taejeon, Rep. of Korea

[21] Appl. No.: 913,782

[22] Filed: Jul. 14, 1992

Related U.S. Application Data

[60] Continuation of Ser. No. 635,461, Feb. 1, 1991, abandoned, which is a division of Ser. No. 221,951, Jul. 22, 1988, Pat. No. 5,068,184, which is a continuation-in-part of Ser. No. 78,745, Jul. 28, 1987, abandoned.

[51] Int. Cl.$^6$ ................................................. A23L 1/221
[52] U.S. Cl. ............................................ 426/650; 426/655
[58] Field of Search ...................... 426/650, 655

[56] References Cited

U.S. PATENT DOCUMENTS 1,010,043  11/1911  Gowen .

FOREIGN PATENT DOCUMENTS 0052001  5/1982  European Pat. Off. .

OTHER PUBLICATIONS

Merory, Food Flavorings, 1960, Avi: Westport, Conn., pp. 132–151.

Winton et al, The Structure and Composition of Foods, vol. IV, 1939, John Wiley & Sons, Inc.: New York, pp. 308–318.

Cervera, E., and Madrigal, R., (Abstract) Environ. Exp. Bot. (1981) 21:441.

Dodds, J.H., et al., in "Plant Tissue Culture" (1986) *Cambridge University Press*, pp. 54–69 & 180–188.

Dougall, D.K., in "Adv. in Experimental Med. and Biol." (1980) (J. Petreciana et al., eds.) *Plenum Press*, N.Y., pp. 135–152.

Dziezak, J.D., *Food Technology*, (Apr. 1986):122–129.

Jalal, M.A.F., et al., *New Phytol.*, (1979) 83:343–349.

Jarret et al., *Plant Genetic Resources Newsletter*, (1984) 57:25–27.

Knuth, M., (Abstract) *Symposium on Biogeneration of Aromas* (1985) No. 121.

Romagnoli, L.C., and Knorr, D., *Food Biotechnology*, (1988) 2(1):93–104.

*Primary Examiner*—Leslie Wong
*Attorney, Agent, or Firm*—Heller Ehrman White; White & McAuliffe

[57] ABSTRACT

A vanilla flavor composition produced by vanilla-plant callus cells suspended in tissue culture, under conditions which promote secretion of vanilla flavor components into the culture medium. The flavor components may be separated from the medium by adsorption resins. Also discussed are methods for preparing callus cells capable of secreting flavor components in tissue culture, and callus cells produced thereby.

17 Claims, 3 Drawing Sheets

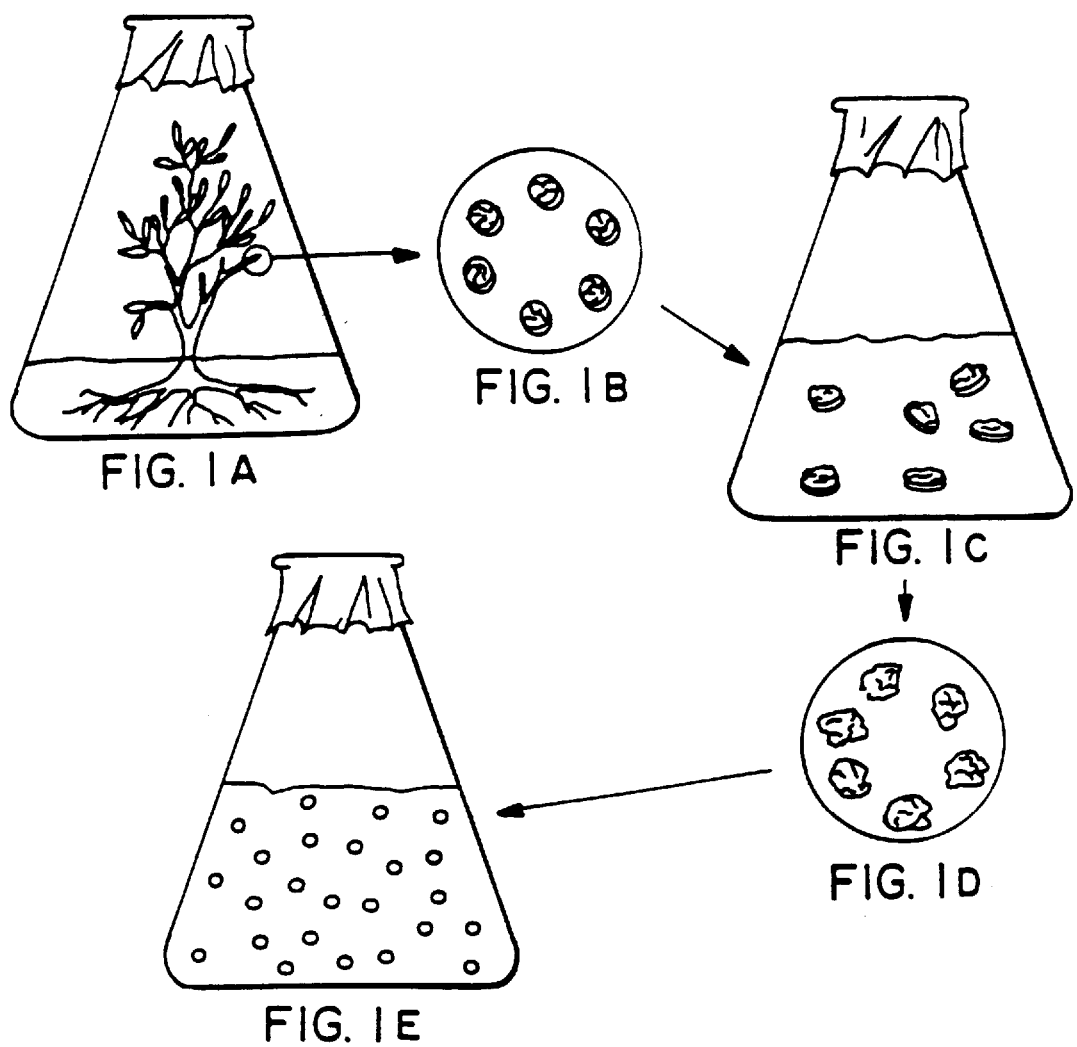
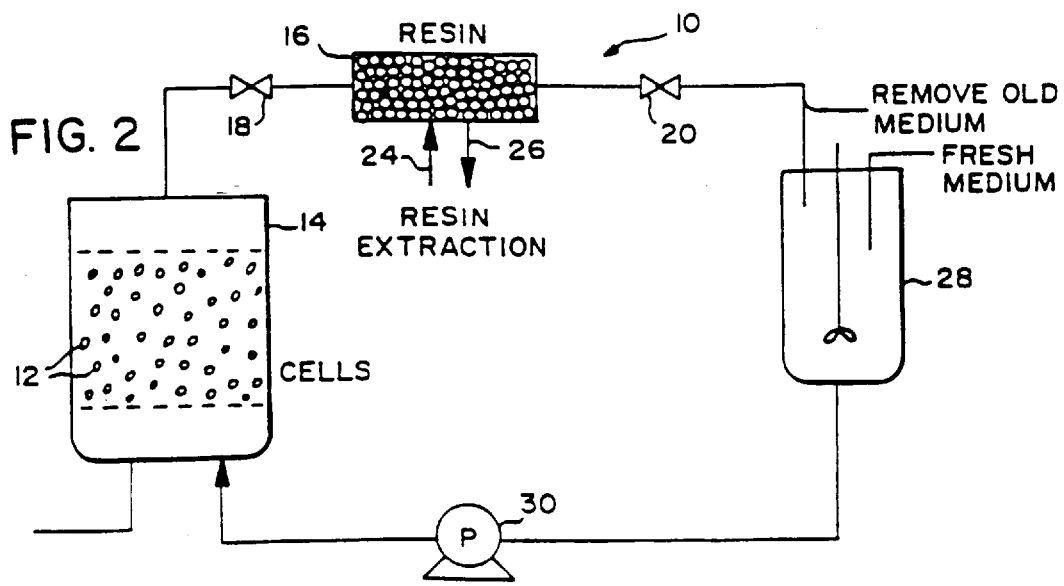

1. 4-hydroxybenzyl alcohol
2. 3,4-dihydroxy benzoic acid
3. vanillyl alcohol
4. 3,4-dihydroxy benzaldehyde
5. 4-hydroxy benzoic acid
6. 4-hydroxy benzaldehyde
7. vanillic acid
8. caffeic acid
9. vanillin
10. coumaric acid
11. ferulic acid

RIPE VANILLA BEAN FLAVOR PROFILE

VANILLA TISSUE CULTURE FLAVOR PROFILE

FLAVOR COMPOSITION

This application is a file-wrapper-continuation of application Ser. No. 635,461 filed Feb. 1, 1991, now abandoned, which is a division of application Ser. No. 221,951 filed Jul. 22, 1988, now U.S. Pat. No. 5,068,184 issued Nov. 26, 1991, which is a continuation-in-part of application Ser. No. 78,745 filed Jul. 28, 1987, now abandoned. This Application is also related to Ser. No. 428,482, filed Oct. 30, 1989, now U.S. Pat. 5,057,424, issued Oct. 15, 1991 as a continuation of Ser. No. 78,745, filed Jul. 28, 1987, now abandoned.

FIELD OF THE INVENTION

The present invention relates to plant-produced flavor compositions and methods, and in particular, to a vanilla flavor composition produced by plant cells in culture. The full citation of references mentioned in parenthesis in the Background below is listed in the Appendix following the detailed description section of this Specification.

BACKGROUND OF THE INVENTION

Natural vanilla is a complex mixture of flavor components extracted from the beans of vanilla plants, usually *Vanilla fragrans*. The extraction process involves an initial curing process, during which vanilla-precursor glucosides in the bean break down to form natural vanillin (4-hydroxy-3-methoxybenzaldehyde) and related flavor components, followed by one of more alcohol extractions to remove the relatively hydrophobic flavor components from the bean. Each of these steps may be relatively time-consuming and costly. For example, the curing process typically is carried out by alternately sun-drying and fermenting the beans, followed by additional warehouse curing and dehydration. Total curing times of up to 4 months may be required to obtain the proper flavor and reduce moisture content to prevent molding. Following curing, the beans are crushed for extraction. Best results are obtained when the crushed beans are extracted with a series of progressively more dilute alcoholic solutions. Each extraction requires a minimum of about 5 days.

Because of the relatively high cost involved in growing, harvesting, and extracting vanilla beans, most vanilla flavor "extract" which is sold commercially is synthetic vanillin, made from wood pulp lignin or from clove oil. The synthetic flavor which makes up about 90% of the vanilla flavor market, however, lacks many of the secondary components which contribute to the quality of flavor and aroma of natural vanilla extract.

One potential alternative source of a complex vanilla flavor composition is plant cells or tissue grown in culture. The possibility of obtaining secondary plant products, including plant flavor components, from cell or tissue culture has been previously proposed (Staba; Zenk; Dougall; Yeoman; and Collin). This approach has been limited, however, by problems of obtaining suitable cell or tissue material for culturing. Studies with a variety of plant types, particularly those which produce essential flavor oils, such as lemon, mint, avocado, and herbs, such as anise, fennel, and sage, indicate that undifferentiated plant tissues are unable to produce the natural oils, possibly because the tissues lack oil glands, and/or because essential metabolic precursors are not produced (Collin). In cultured herb tissues, flavor components reappeared following redifferentiation into roots and shoots (Becker), and in both celery and onion, flavor components reappeared with redifferentiation (Al-Abta; Selby; Turnbul).

Related to this problem is the difficulty of obtaining cell or tissue material that can be expanded readily in culture, produces the secondary products in high yield, and is stable with long-term culturing. In particular, differentiated or partially differentiated cultures generally do not grow well in culture. Even where such cultures are obtained, the level of secondary product formation may be quite low compared with the natural plant, and therefore poorly competitive with natural flavor extraction methods.

It must be noted that certain plant types, particularly orchids, do not readily form true undifferentiated callus that is capable both of continuing cell growth and of producing fine suspensions. Vanilla plant is an orchid; formation of stable, undifferentiated callus capable of forming suspensions from this plant has not been reported.

The problem of obtaining flavor material in an easily isolatable form from cell culture has also limited the cell culture approach. In some cases, flavor component(s) may not be secreted from the culture cells, such that the flavor components must be harvested from the cell or tissue material. By way of example, U.S. Pat. No. 3,710,512 describes a method for producing a licorice extract-like material from cultured plant tissue cells suspended in a culture medium. Here the flavor composition is extracted by boiling the culture mix, to release the compound from the cells, filtering the boiled material, to remove cell debris, and concentrating the filtrate. It can be appreciated that product extraction is inefficient both because cells are lost and because the flavor material must be purified from total cell extract material.

In summary, although the possibility of obtaining flavor components in plant cell or tissue culture has been explored, difficulties in obtaining plant cell or tissue material which is capable of (a) growing readily in culture, over long periods, and (b) secreting desired flavor components in a form which allows isolation from the culture medium, have severely constrained this approach.

SUMMARY OF THE INVENTION

One general object of the invention is to provide plant cells capable of producing and secreting flavor components in culture.

A more specific object of the invention is to provide such cells which produce and secrete a complex vanilla flavor composition. A related object of the invention is to provide methods for obtaining callus cells which are capable of long-term growth in culture and which produce and secrete flavor components into the culture medium in easily isolatable form.

Yet another object of the invention is to provide a plant cell culture system for use in the efficient production of vanilla flavor components.

Providing a novel vanilla flavor composition which is produced in cell culture is still another object of the invention.

The invention includes, in one aspect, a vanilla flavor composition produced in culture by callus cells which are derived from Vanilla plant tissue material, and selected for ability to propagate in plant liquid culture medium as suspensions. The callus cells are cultured under conditions which promote secretion of vanilla flavor components into the medium, and the secreted flavor components are separated from the medium.

The callus cells may be prepared from tissue segments taken from the growing point of a Vanilla plant, such as *V.*

*fragrans* or *V. phaeantha*, by first culturing the tissue segments on a solid support, in the presence of plant growth hormones, and selecting those tissue segments which show partially differentiated callus like structures.

Since true callus formation from these structures occurs with an extremely low frequency, the callus like tissues, according to one feature of the invention, are subjected to environmental stress. Thus, true callus cells from *Vanilla sp.* may be obtained by submerging differentiated or partly differentiated structures in a liquid medium with restricted gas exchange for long periods of time (for example, 1–2 months) and then plating out the tissue segments onto solid agar medium containing appropriate growth hormones. The callus material is then broken up and cultivated while suspended in the liquid medium. Clumps of cells, 1 mm to 6 mm in diameter are formed. Fine suspensions with the ability to grow rapidly in liquid cultures can be produced by continually selecting and transferring fine cell aggregates or by manipulating hormones in liquid media. These cells are capable of producing and secreting vanilla flavor into the liquid medium.

In one embodiment, the cells produced are derived from *V. fragrans* and have the characteristics of ATCC (American Type Culture Collection) No. 40354. The cells may be further selected, e.g., by plating on solid agar medium, for high vanillin production.

According to another aspect of the invention, it has been discovered that vanilla flavor production is enhanced in a cell culture by continually removing flavor components from the culture medium. This can be done efficiently by contacting the culture medium with an adsorbent, such as phenolic resins or activated charcoal, which adsorb the flavor components. The flavor components are easily extracted from the adsorbent.

One vanilla flavor composition which has been produced according to the invention has a ratio of vanillin to the combined amounts of vanillyl alcohol, 3,4-dihydroxybenzaldehyde, 4-hydroxybenzyl alcohol, and 4-hydroxybenzaldehyde, which is substantially greater than that of natural vanilla extract obtained from vanilla beans. This composition is also characterized by a ratio of vanillin to the combined amounts of flavor components which elute later than vanillin on an HPLC column eluted with a methanol/acetic acid gradient, which is substantially less than that of natural vanilla extract obtained from vanilla beans.

In another aspect, the invention includes callus cells which are (a) capable of growth in cell culture, (b) produce and secrete a selected plant flavor component in the cell culture, and (c) are preferably undifferentiated. In one embodiment, which includes callus cells derived from vanilla plant tissue material, the amount of flavor material secreted in the cell culture is enhanced by removing the secreted flavor material from the culture medium as it is produced by physical adsorption. An exemplary vanilla plant callus cell has the characteristics of ATCC No. 40354.

Also forming part of the invention is a method and cell culture system for producing plant flavor composition. The system includes a culture chamber, where cell growth and flavor component production occur, and a separate extraction chamber where the flavor components are extracted from the medium, by circulating medium from the culture chamber through an adsorbent in the extraction chamber. The cells are preferably retained in the culture chamber, e.g., by cell immobilization on a porous substrate.

These and other objects and features of the invention will become more fully apparent when the following detailed description of the invention is read in conjunction with the accompanying drawings.

BRIEF DESCRIPTION OF THE DRAWINGS

FIGS. 1A–1E illustrate plant tissue manipulation steps used in producing callus cell particles capable of producing and secreting vanilla flavor components in liquid culture;

FIG. 2 is a diagrammatic representation of a reactor system used in producing vanilla flavor components, according to one aspect of the invention.

BEST MODE OF THE INVENTION

I. Preparation of Callus Cells

Figure 3A:
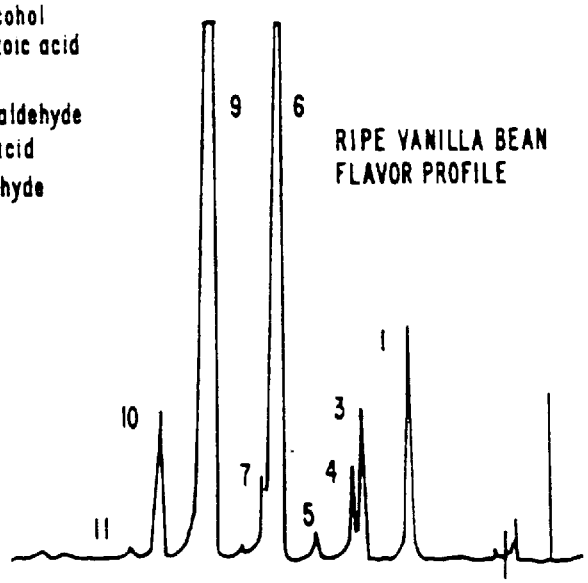
FIGS. 3B and 3A are HPLC chromatograms of vanilla flavor components of the invention and of natural vanilla extract obtained from vanilla beans, respectively.

Part A below and Examples 1 and 2 below describe the preparation of callus cells from the growing root tips of sterilized plants, according to a novel callus-induction method of the invention. In part B and Example 3, the preparation of callus cells from sterilized vanilla beans is described. Methods for selecting high-producer cells are considered in Part C.

A. Preparing Callus Cells from Growing Plant Tips

A variety of vanilla plant species, including *V. fragrans, V. phaeantha, V. pompona,* and *V. tahitensis*, may be used for preparation of callus cells, although *V. fragrans* and *V. phaeantha* are preferred. These plants may be obtained from commercial sources, such as the U.S.D.A Research Station (Puerto Rico) or San Francisco State University.

In addition, studies conducted in support of the present invention have shown that tissues from certain fruit-producing plants also produce vanillin and related flavor components in culture. These products have been observed in cultures of callus tissue derived from vegetative and non-vegetative parts of peach, strawberry, grape, apple and apricot plants.

In general, the callus material from these fruit-producing plants can be obtained by conventional procedures which do not necessarily involve the callus-stressing step used herein for obtaining callus from vanilla plants. The invention thus further includes a method of producing vanillin and related products by culturing callus derived from fruit-producing plants.

To obtain sterilized, bacteria-free vanilla plants, the plants are grown to maturity under controlled greenhouse conditions, such as those described in Example 1. Vegetative shoots harvested from the plants, with expanded leaves removed, are sterilized and cultured with repeated transfer on agar plates containing a suitable growth medium and an antibiotic. Explants which show no sign of contamination are grown under conditions which promote adventitious bud formation. Details of the procedure, which provided about 80% bacteria-free explants, are given in Example 1.

One method for obtaining callus cells, according to the invention, is detailed in Example 2, and illustrated in FIG. 1. In this method aerial root tips are cut from the above sterilized explants (FIG. 1A), sterilized, and cut into 3–4 mm root sections which are then individually cultured on solid agar medium containing selected growth hormones. One optimal medium contains Murashige-Skoog (MS) medium (Dodds) supplemented with 1 ppm each of 2,4-dichloroacetic acid (2,4-D) and benzylacetic acid (BA).

The root sections are transferred 2–3 times onto the same medium, and the segments are examined for callus formation, as evidenced by formation of amorphous cell clumps on the cut surface of the segment, illustrated in FIG. 1B. Typically less than 0.1% of the root sections which were handled in this way showed evidence of true callus formation.

To substantially improve the frequency of true callus formation form the above, root sections with callus-like swellings or callus-like structures are submerged in a liquid medium of a defined composition for extended periods of time (for example, 1–2 months) (FIG. 1C) There is little or no tissue growth during this period. When this material is plated out on a solid medium of similar composition, true undifferentiated callus is formed (FIG. 1D). The frequency of true callus formation thus is improved from less than 0.1% to 100%.

A typical medium composition for the liquid submergence step (FIG. 1C) and for subsequent transfer to solid medium (FIG. 1D) is given in Example 2. An exemplary growth hormone mix includes 1 ppm 2,4-D and BA.

It is to be noted that liquid submergence with restricted gas transfer may be a stress stimulus that causes a differentiated, organized plant tissue to dedifferentiate. Other possibilities for inducing such a response could include temperature shock and nutrient stress when used in conjunction with or independent of the liquid submergence step.

To obtain an actively dividing cell culture in liquid medium, the calli from above are broken up as by mincing into relatively small pieces, which are then suspended in liquid growth medium (FIG. 1E), such as the one used in the solid-medium culture, and the pieces are incubated with agitation until the calli gradually break down into small multi-cell clumps, typically containing 5–20 cells. Since the objective at this stage is to increase the cell biomass rapidly, the nutrient medium contains adequate carbon and nitrogen sources, as well as auxin and cytokinin growth hormones, such as 2,4-D and BA, as above. The cells are cultured under standard plant culture conditions until the cells reach the end of the logarithmic growth phase, typically at a cell concentration of about 7–8 g/l. The cells are now examined for cell viability, by uptake and cleavage of a fluorescent dye precursor. If more than about 25% of the cells are viable, the cells are reduced by centrifugation, and resuspended in fresh growth medium, at a concentration of about 2–3 g/l. One cell line which has been prepared by this method has been deposited at the American Type Culture Collection, Rockville, Md., and has ATCC No. 40354.

The cells obtained in the method are classed as undifferentiated, on the basis of (a) rapid cell growth in culture and (b) lack of identifiable differentiated cell structures, as observed by light microscopy.

B. Preparing Callus From Seeds

Beans from vanilla plants, including the species listed above, are suitable for the present method, and can be obtained from the sources named above. Initially, the beans are sterilized, cut in half, and grown on suitable germination agar medium, such as the one used in Example 4. A portion of these seeds-typically about 5–10%-will germinate, as evidenced by the production of embryo and subsequent formation of a cone-shaped protocorm.

Continued growth of the germinated seeds, with transfer to fresh agar plates containing a suitable hormone-supplemented growth medium, such as described in Example 4, produces numerous rhizoids formed from the epidermal cells of the of embryo and leak primordia on top of the corn-shaped protocorms. Segments of both the leaf primordia and rhizoid tip segments are individually cultured on agar plates containing a medium similar to one described in part A above.

The tissue pieces are cultured for 2 to 3 generations of 3–4 weeks each on the agar medium, submerged in a liquid medium for 4–8 weeks and then plated back on solid medium of a similar composition to form true callus.

The calli may be teased apart and cultured directly in plant liquid growth medium like that above. Alternatively, in cases where cell growth is slow, callus friability is further improved through intermediate liquid culture and solid-medium culture steps. Liquid cultures of actively growing callus cells (now called suspensions) are grown to stationary phase, and tested for cell viability, as above. Viable cell cultures are subcultured to a desired cell density in the liquid medium.

C. Selecting High Flavor-Component Producers

The callus cells produced above can be further selected to obtain high producers of vanillin and/or other selected vanilla flavor components. The selection method may follow known radioimmunoassay (RIA) methods (Weiler), using radiolabel or fluorescent-label antibody methods to identify a selected flavor component, e.g., vanillin. Here the flavor component is attached to a carrier protein, for example keyhole limpet hemocyanin, and used to induce antibodies in an inoculated animal, yielding a serum antibody fraction that forms one of the reagents for the assay. The second reagent is a fluorescent-labeled anti-IgG antibody specific against the first-reagent anti-bodies. Thus, if the serum antibody fraction is obtained from goats, the second reagent is a labeled anti-goat IgG antibody. The second reagent is commercially available.

In the assay procedure, the cell or cell clumps from above are plated on solid agar medium containing suitable nutrients for vanillin production, as considered in Section II. After 1–2 days culture on the plates, the cell clumps are reacted with first-reagent serum antibody from above, to bind antibody to the plated cells in proportion to the amount of vanillin produced by the cells. Adding the second-reagent fluorescent-labeled antibody to the cells now labels the vanillin producers with a fluorescent tag. High producers are identified by high fluorescent levels.

Another type of cell selection involves direct detection of vanillin or other vanilla-related product directly on the agar plates. One preferred assay for detection of vanilla is based on a modification of the vanilla test for flavonoids. In an acid solution, vanilla is protonated to give a weak electrophilic radical which can react at with a flavonoid, such as catechin, at the 6 or 8 ring position, to form a compound which is turns red or pink on dehydration (Sarkar). The assay is applied in the present invention by first plating the cell clumps, at a suitable concentration, on a solid-agar nutrient medium (defined below), and allowing the cells to incubate under conditions of vanillin production. After a 1–2 day incubation period the plates are blotted with a filter paper to transfer cell products. The filter is then sprayed with a catechin reagent containing catechin in an acid solution, and dried by heating at temperatures below about 80° C. The intensity of red-colored spots on the dehydrated filter indicates the extent of vanillin production by the corresponding cell clumps. Those spots identified with highest vanilla production are then picked from the agar plate for further growth and/or cell selection.

The above cell selection procedures can be used to detect natural high vanilla flavor producing variants obtained by somaclonal variation or those induced artificially by chemical or radiation induced mutagenesis and by specific biochemical selection routes (Zenk, Widholm).

II. Producing Vanilla Flavor Composition

A. Cell Culture Media

For producing vanilla flavor composition, the callus cells from above are cultured in liquid medium under conditions which are selected to maximize the amount of vanillin produced and/or to achieve a desired ratio of vanillin to one or more other vanilla flavor components. The principal variables in the medium which can be adjusted to improve yield of the desired vanilla composition are (a) nutrient, (b) plant hormones, and (c) vanilla component precursors. References which review the topic of secondary plant product formation in culture may be consulted for a more detailed discussion of factors which effect culture production (Collin, Dodds).

The nutrients which are present in the medium include a carbon source; nitrogen sources, major salts, minor salts, vitamins and hormones. These nutrients may be those supplied by any conventional plant tissue culture medium. Vanillin production occurs in presence of such a medium, but a preferred production medium limits or eliminates all nutrients, except for a carbon source, calcium chloride and sodium chloride (referred to as a minimal medium). Limiting the availability of certain key nutrients, such as nitrogen, has the effect of inhibiting cell growth and therefore the resources of the cell which are devoted to cell growth alone. At the same time, since the vanilla flavor components do not contain nitrogen, production of the desired components is not inhibited.

The concentration and quality of the carbon source in a defined medium may also affect vanilla flavor production. Some carbon sources, such as glucose, sucrose, fructose and maltose are preferred for cell growth or for combined cell growth and vanilla flavor production, while others such as ribose, galactose, mannose, and xylose, are preferred for vanilla flavor production from non-growing cells.

The effect of plant hormones on production and composition of the vanilla components can be assessed by conventional methods. Experiments conducted in support of the present invention show that the hormone mix containing 2,4-D and BA used in callus cell production and growth are suitable for vanilla flavor production in culture medium. To determine other favorable hormone compositions, the hormone mix may be systematically adjusted to supplement or replace the existing individual hormones with one or more additional plant hormones. For example, 2,4-D may be replaced by indole 3-acetic acid (IAA) or other auxins. Similarly, BA may be replaced by kinetin, zeatin, or other cytokinins. The effects of other plant hormones, including gibberelins and ethylene, may be similarly examined.

After subculturing the cells in altered hormonal medium for 2–3 generations, the cells are grown for a select period, typically 7–14 days, and assayed for cell growth, and for production of vanillin and/or select vanilla flavor components, the latter by HPLC methods detailed below and in Example 12.

It is to be recognized that hormones are essential for cell growth and may affect the quantity and composition of vanilla flavor components in a system combining cell growth with flavor production. However, in systems separating cell growth from vanillin production, the quality of the hormone in the growth medium may affect subsequent vanilla flavor composition in the production medium. The final production medium in itself may not require any hormone supplements, and as indicated before could be a mix of sugar (carbon source), salt (sodium chloride) and calcium chloride.

A third factor influencing vanilla component production is the nature and concentration of vanilla component precursors in the medium.

These precursors may include ferulic acid, phenylalanine, dehydroshikimic acid, vanillyl alcohol either in free form or as glycosylated compounds. The cell culture method is also amenable to induction or inhibition of selected vanilla flavor components by addition of immediate precursors or metabolic inhibitors, respectively, to the medium.

It will also be recognized that temperature, light, pH and gas mixture may also be varied to alter vanilla flavor levels or composition.

In summary, one advantage of the present invention over plant extract methods is the ability to readily manipulate culture conditions to optimize net production and/or relative concentrations of flavor components.

B. Extracting Flavor Components

As indicated above, the callus cells in liquid culture produce and secrete the desired flavor components into the culture medium, allowing the components to be extracted without loss of culture cells, and with a minimum of required purification. According to another important aspect of the invention, it has been discovered that vanilla component production is significantly enhanced by removing the flavor components from the medium by adsorption as soon as they are produced. The greater production observed when the flavors are continuously removed from culture is due in part to product instability in the medium and to removal of feedback inhibition for product synthesis. One preferred method for removing flavor components in culture is to contact the medium continuously with an absorbent such as activated charcoal or a hydrophobic resin which selectively adsorbs vanilla flavor components.

Suitable resins for use in component extraction include polymeric hydrophobic adsorbents, such as XAD-4 and XAD-7 (Rohm and Hass, Philadelphia, Pa.), having non-polar phenolic groups capable of adsorbing the vanilla flavor components. Activated charcoal from various commercial sources is also an excellent adsorbent that leads to large increases in the accumulation of vanillin and other vanilla flavor components.

Examples 8 and 9 illustrate the effect of activated charcoal amount on production of vanilla flavor components for a complete medium with the full complement of salts, vitamins, hormones, micronutrients and a nutrient deficient minimal medium.

In the simplest configuration, resin or activated charcoal is included in the culture reaction vessel. After culture, the resin beads are washed several times with distilled water, then extracted with an alcoholic solution, typically 50% alcohol, to remove the vanilla flavor components. Alternatively, the resin may be packed in a column, and the flavor components eluted with a solvent gradient, to obtain separate product components. The eluted flavor components can then be recovered in more concentrated form by solvent evaporation, if desired. The nature of the flavor components obtained in a typical culture production method, according to the invention, is described below.

In a second general method, cell culture production and product extraction are physically separate and the culture medium is periodically contacted with adsorbent material to remove accumulated flavor products. In a simple, discontinuous system, this can be done by applying a cell culture mixture periodically to a resin column, eluting unbound material with several washes of distilled water, and then eluting bound flavor material, as above, with an alcoholic solution or gradient. A continuous system, in which the callus cells are immobilized in a reaction chamber, and culture medium is continuously circulated through a resin bed is described below.

Vanilla flavor material may also be isolated from the culture cell mixture, or cell-free culture medium, by direct solvent extraction.

C. Continuous Culture System

FIG. 2 illustrates, in simplified form, a culture system 10 designed for continuous, large-scale production of vanilla flavor composition, using the method of the invention. The callus cells in the system, here indicated at 12, are immobilized or retained within a culture chamber 14 to allow circulation of culture medium through the chamber. A variety of methods are available for immobilizing the cells within the chamber. In one preferred method, the cells (or cell clumps) can be encapsulated or entrapped using polymeric matrices, such as sodium alginate, agarose, agar, kappa-carageenen, or chitosan.

In another embodiment, the cells are confined within the chamber by suitable filtration means. This may include small-pore filters placed at the inflow and outflow ports of the chamber, or use of hollow fibers for cell culture, as described in U.S. Pat. No. 4,442,206.

Also contained in the system is a resin chamber 16 which is connected in-line with the culture chamber, through a valve 18, for extracting product carried in culture medium. Resin in chamber 16 is immobilized on a solid support conventionally. Flow of culture medium out of the chamber is through a valve 20. The cell product material bound to the resin is periodically extracted by closing valves 18, 20, and passing extraction solution through the chamber via extraction ports 24, 26.

Following product extraction in the resin chamber, a portion of the medium is removed, and the remainder flows into a mixing vessel 28, where the medium is mixed with fresh medium supplied to the system, as shown. From here, the medium is returned to the culture chamber, through a pump 30 which produces the circulation of medium in the system, preferably at a rate which circulates about 80% of the medium every hour. It will be appreciated that the system is equipped with temperature controls and gas supplies for maintaining the system at selected environment conditions.

III. Vanilla Flavor Composition

Figure 3B:
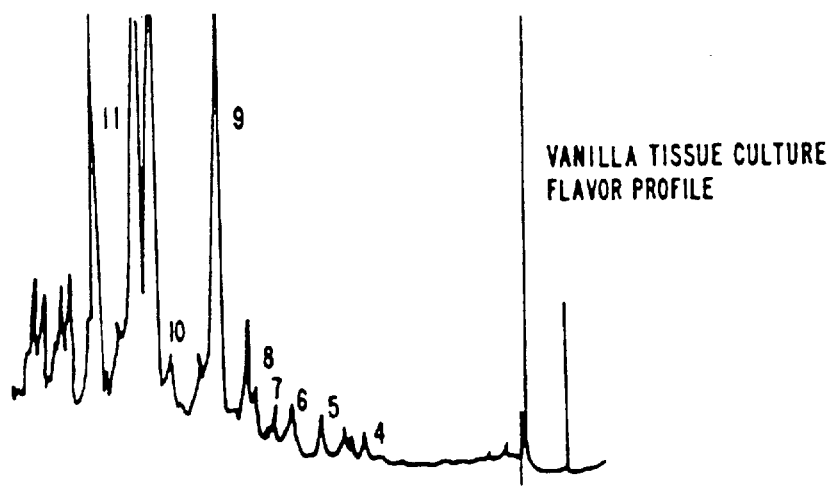

FIG. 3B shows an HPLC chromatogram of a typical vanilla flavor composition produced according to the invention, as detailed particularly in Example 7. HPLC chromatographic conditions are given in Example 12. As seen, the composition includes a predominant vanillin peak (peak 5) and four earlier-eluting peaks which are identified as 3,4-dihydroxybenzaldehyde (peak 1), 4-hydroxybenzoic acid (peak 2), 4-hydroxybenzaldehyde (peak 3) and vanillic acid (peak 4). In addition, the composition contains a number of slower-eluting components.

Figure 4:
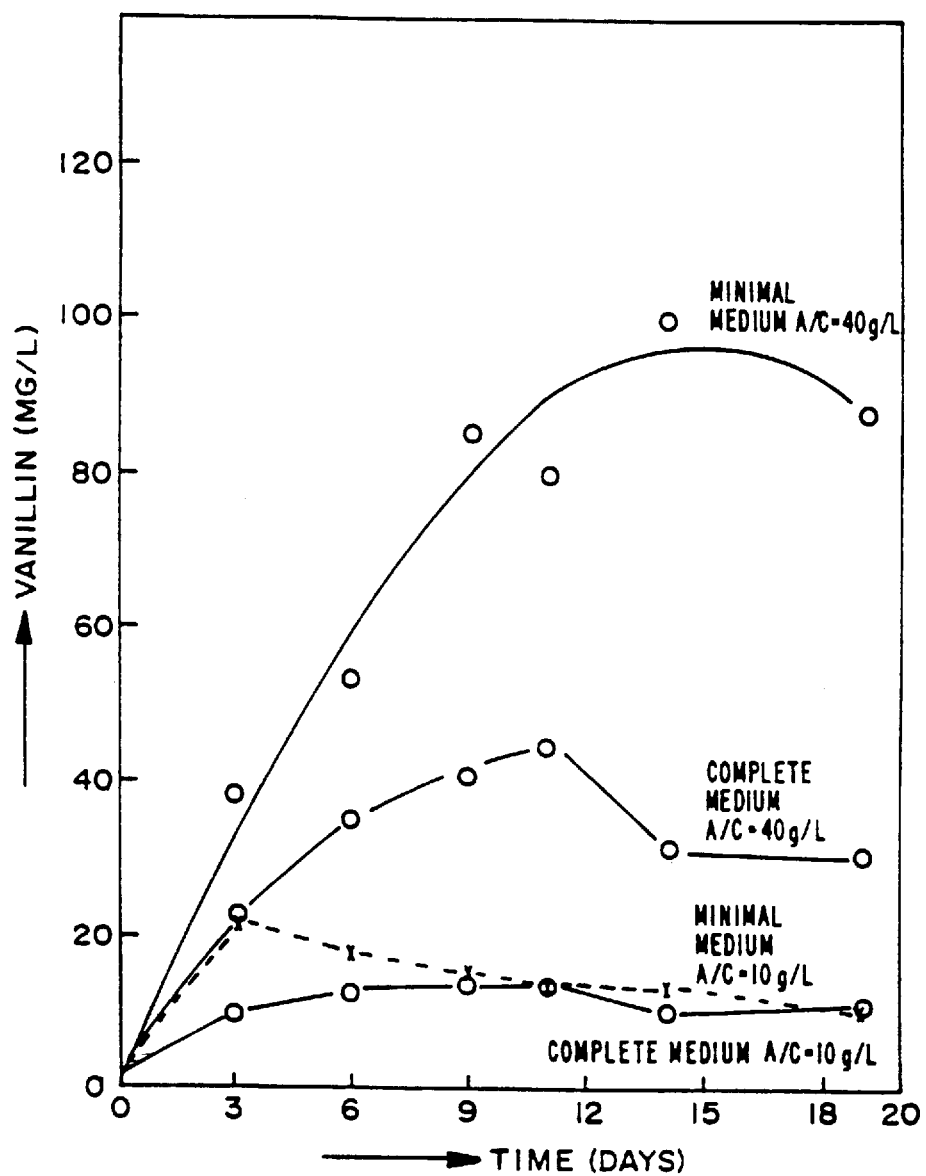
FIG. 4 shows the time-course of vanillin production by vanilla suspension cultures as a function of medium composition and activated charcoal concentration.

The HPLC profile of natural vanilla extract obtained from vanilla beans is shown in FIG. 4. This composition also has a predominant vanillin peak, and includes the components identified with peaks 1–4 in FIG. 3A. A comparison of the two compositions shows that the vanilla composition of the invention has a greater ratio of vanillin to the compounds corresponding to peaks 1–4 than the natural vanilla bean extract. On the other hand, the ratio of vanillin to slower migrating components (those eluting after vanillin on the HPLC column) is smaller in the composition of the invention than in the natural vanilla extract. These ratio comparisons are with reference to the HPLC chromatography conditions employed, as detailed in Example 12.

The HPLC analysis provides a convenient method for following changes in the relative amounts of components in the vanilla composition with changes in culturing conditions, such as variations in hormone, metabolic precursors, or nutrients in the culture medium. For example, to enhance the relative concentration of any selected component, the medium may be supplemented with precursor or inhibitor compounds, and the effect relative composition of the component easily assessed. Additionally, cells which secrete a desired ratio of flavor compounds can be selected on the basis of the HPLC profiles of their products. Also, chromatography can be used to achieve a desired purification of the composition, for example, to remove all or selected peaks which elute after the major vanillin peak.

The vanillin composition of the invention may be formulated as a composition, preferably in an ethanolic solution similar to natural and artificial vanilla flavor compositions sold commercially. The flavor components can also be added to processed foods, such as baked goods, beverages, ice cream, and the like, for natural vanilla flavor.

From the foregoing, it can be appreciated how various objects and features of the invention have been achieved. The callus cells obtained using the novel plant tissue culture methods described in Section I have several advantageous features which are unexpected in view of earlier studies on secondary product production by cultured plant cells or tissues. In particular:

A. The vanilla flavor-producing vanilla cells are substantially undifferentiated, and therefore allow rapid cell increase in cell culture, for achieving a biomass adequate for large-scale vanilla flavor production.

B. The vanilla callus cells are stable in liquid cultures under both cell-growth and vanilla production conditions. Studies carried out in support of the invention show continued ability of vanilla cells to produce vanilla flavor components in subculture after several months, and the cells can be expanded in growth medium repeatedly without loss of vanilla flavor producing ability.

C. The cells derived from the bean or from vegetative parts of the vanilla plant produce a complex flavor mixture containing all or most of the flavor components produced by natural vanilla bean only after complex curing processes.

D. The cells secrete the flavor components, allowing efficient isolation and purification of the composition without depleting either the cell medium or cells in the production culture.

According to another important feature of the invention, the amount of flavor composition produced can be enhanced significantly by removing flavor components from the medium as they are being produced. This can be done in a culture system containing cells, medium and the adsorbent intimately mixed and aerated, or an alternate system in which the cell medium is circulated through an adsorbed bed adapted to adsorb hydrophobic product compounds from the medium. The adsorbed material, in turn, can be readily extracted from the resin. This feature, and the ability to grow the cells rapidly and stably in culture, allow for efficient, and large-scale production of vanilla flavor compounds in culture. Further, the nature of the flavor composition can be altered, to enhance selected flavors and/or inhibit others, by varying culture conditions.

Finally, the callus cells can be selected for high production and/or enhanced production of specific flavor components by cell selection.

The following examples illustrate various methods of preparing callus tissue for vanilla composition production in culture, culture conditions for achieving production, and methods of obtaining the extract. The methods are intended to illustrate, but not limit the scope of the invention.

EXAMPLE 1

Propagation of Vanilla Plants

A. Establishing greenhouse plants

Two species of vanilla plants, V. fragrans, and V. phaeantha, were planted in a mixture of soil, peat moss, and milled bark (1:2:2 by volume). The vines were grown upright, with the aerial roots clinging to stakes and sphagnum-moss wall support. The vines were misted daily with a sprinkler system, and a complete fertilizer was applied once a month. The greenhouse humidity was maintained at between about 40–80%, and the temperature, between about 20°–29° C., taking care to avoid direct exposure to sunlight.

B. Sterilizing plant tissue

Vegetative shoots, about 5 cm in length, were harvested from the greenhouse plants, and the expanded leaves removed from the shoots. After soaking the shoots in 1% Alconox for 20 minutes, with occasional shaking, and rinsing three times in distilled water, 3 mm shoot tips were removed by dissection, and the remaining shoot was cut into approximately 1.5 cm nodal segments, such that such that each segments includes one node. The shoot tips and nodal segments are placed upright in 1% agar containing MS (Murashige-Skoog) medium supplemented with 1 ppm BA (Medium A) and 500 ppm cefotoxime. Removing the epidermal layers of the nodal segments at this stage increased the number of bacteria-free tissue segments which are obtained. After culturing for 7–10 days at about 28° C., the shoot tips and nodal segments were transferred to fresh Medium A agar plates supplemented with 250 ppm cefotoxime. This transfer procedure was repeated 3 times.

C. Propagation of sterile plants in vitro

Explants which showed no signs of contamination were grown on agar containing MS medium supplemented with 500 ppm casein-hydrolysate, and 0.5–1.0 ppm BA for adventitious bud proliferation (Dodds). The individual buds which formed were cultured on agar plates containing MS medium supplemented with 0.15 ppm each of NAA and BA or kinetin for plant development. The above disinfestation procedure yielded about 80% bacteria-free explants.

EXAMPLE 2

Callus Induction—Method 1

Aerial root tips, 1–2 cm long, were cut from the sterile explants from Example 1, and surface sterilized with 10% Clorox® solution for 1–2 minutes, followed by 3 rinses in sterile distilled water. The root sections were cut into 3–4 mm segments, and the segments were individually cultured on 0.8% agar containing MS medium supplemented with 1 ppm each of 2,4-D and BA. A total of about 3,000 root segments from each of the V. fragrans and V. phaeantha plants were cultured.

After about 4 weeks in culture, at 28° C. and under ambient atmosphere, most of the segments showed elongation of the root tips. These swelled root segments were transferred 2–3 times to fresh solid medium containing MS and 1 ppm each of 2,4-D and BA, about 2–3 weeks per transfer, producing a small number of root segments (about 3 out of a total of the 3,000 cultured) which showed formation of true callus. The frequency of callus formation in both V. fragrans and V. phaeantha using the above procedure was of the order of 0.1%.

EXAMPLE 3

Callus Induction—Method 2

Root segments obtained from V. fragrans and V. phaeantha explants were cultured on 0.8% agar containing MS medium and $E_4$ vitamins (see Table 1) supplemented with 1 ppm each of 2,4-D and BA at 28° C. After 8 weeks, the growing root sections were transferred to fresh agar plates of a similar medium composition for a further 4 weeks. The swollen differentiated root structures (6–8 pieces) were then transferred to 250 ml flasks containing 125–150 ml liquid media. The composition of the liquid medium was identical to that of the solid medium with the exception of the agar. The pieces were completely submerged in the liquid and shaken on a rotary shaker at a speed of 150 revolutions/min. at a temperature of 28° C. for a period of 2 months. Each piece was then cut into 4 sections and plated onto a solid medium with identical nutrient supplements as before. Twelve days later, friable "true" callus was obtained from every one of the above pieces, indicating a callus formation frequency of 100%. Each callus piece was dissected into 4–5 smaller pieces and transferred to fresh agar medium. Rapid callus growth was obtained on each plate. A 5–6 fold increase in tissue fresh weight over a 4 week period was observed. The above produced callus was subcultured on a 4–6 week interval and was shown to maintain its growth rate on each subculture.

TABLE 1

$E_4$ Vitamin Composition

| | mg/L | | mg/L |
|---|---|---|---|
| Myo-inositol | 100 | D-Ca-Pantothenate | 0.5 |
| Nicotinic acid | 2.5 | Riboflavin | 0.25 |
| Pyridoxine. HLC | 1.0 | Ascorbic Acid | 0.5 |
| Thiamine. HLC | 10.0 | Choline chloride | 0.1 |
| Glycine | 0.5 | L-cysteine HCL | 1.0 |
| Folic Acid | 0.5 | Malic Acid (monosodium salt) | 10.0 |
| D-Biotin | 0.05 | Casein Hydrolygate | 50.0 |

TABLE 2

Hormone Composition 5 uM 2,4-D + 5 uM BA
5 uM 2,4-D + 1 uM BA
20 uM 2,4-D + 5 uM kinetin
10 uM 2,4-D + 1 uM kinetin

EXAMPLE 4

Callus Induction—Method 3

A. Seed germination

Individuals beans of V. fragrans, and V. phaeantha were washed thoroughly in distilled water, then soaked in 1% Alconox solution for 20 minutes with occasional shaking. After rinsing three times with distilled water, the seeds were soaked in a 10% Clorox® solution for 20 minutes with occasional shaking, then rinsed 3 times with sterile distilled water.

The sterilized seeds were cut in half longitudinally, and cultured with placental residues and sticky fatty materials with 95% alcohol on Knudson medium, supplemented with 10% fresh coconut water. The seed cultures were maintained at 32° C. in the dark for periods up to 4 months. The first evidence of seed germination is the rupture of the black seed coat, followed by protrusion of the spherical and then cone-shaped embryo, and subsequent formation of a cone-shaped protocorm. The percentage of seeds which germinated was about 6%.

B. Callus formation

After germination, the seeds from above are transferred to fresh agar plates containing Knudson medium supplemented with the vitamin mixture given in Table 1 above, and a growth hormone mixture containing various combinations of 2,4-D and BA. The seeds are grown in subdued light at 32° C. for a period of about 4 weeks, under ambient atmosphere. During the period of growth and development, numerous rhizoids formed from the epidermal formed from the epidermal cells of embryos and leaf primordia on the top of the cone-shaped protocorms.

Segments of leaf primordia cut from the tops of the protocorms, and rhizoid tip segments cut from the developing protocorms (each about 2 mm in length) are individually cultured on 0.8% agar containing MS medium supplemented with 1 ppm each of 2,4-D and BA.

After about 4 weeks in culture, the leaf primordia and rhizoid segments are transferred 2–3 times to fresh solid medium containing MS and 1 ppm each of 2,4-D and BA, about 2–3 weeks per transfer, producing a small number of segments which showed callus-like structures. These callus-like structures from the solid-medium culture are teased apart, or chopped, depending on consistency, to approximately 0.5–1 gram pieces, transferred to 250 ml Erlenmeyer flasks, and covered with 100–150 ml liquid medium identical to one described above, except for the absence of agar, for a period exceeding 1 month. The pieces, when transferred to solid media of similar composition, form true undifferentiated callus.

EXAMPLE 5

Formation of Cell Suspensions

The calli obtained in Example 3 were transferred to 0.8% agar containing MS medium, 3% sucrose, the vitamin mix given in Table 1 below, and one of the combinations of plant growth hormones listed in Table 2. The calli were cultured in subdued light at about 28° C., under ambient atmosphere, and subcultured approximately every 4–6 weeks, a total of 1–4 times.

These calli were teased apart or chopped, depending on consistency, to approximately 0.5–1.0 gm pieces, and these were transferred to 250 ml Erlenmeyer flasks, and covered with 50 ml liquid medium identical to that described above, except for the absence of agar. The flasks were covered with a sterile cap, and incubated with stirring for 30 days under ambient atmosphere. Stirring speed was about 150 rpm, and incubation temperature was between about 24°–30° C. The callus clumps are reduced slowly under these conditions of small, multi-cell particles containing less than about 10 cells/particle.

Before the stationary phase was reached (about 2 weeks in liquid culture), the cells were examined for cell viability, according to the method described below. If cell viability was greater than about 25%, and if the cell suspension revealed an increase in cell density, the fine multi-cell particles were drawn off by pipetting, condensed by low-speed centrifugation, and added to fresh liquid culture for subculturing under the above conditions. Larger cell clumps remaining in the original culture were broken down by addition of fresh medium to the clumps remaining in the flasks, and further stirring under the same culture conditions. The cells were assayed for viability as above, and small multi-cellular particles from the two subcultured groups were drawn off, condensed, and subcultured in fresh medium as above. The fine-particle suspension of cells could be subcultured in this fashion to high cell densities.

Cell viability of the callus cell suspension was examined by dye exclusion of a fluorescent dye. A stock solution of fluorescein diacetate (FDA) stain (5 mg FDA/ml acetone), was diluted 1:50 with cell culture medium and one drop of the diluted stain added to one drop of cell suspension on a microscope slide. Viable and non-viable cells were counted by fluorescence microscopy.

EXAMPLE 6

Producing Vanilla Flavor Composition

The cultured suspensions of *V. fragrans* from Example 5 were grown to a cell concentration of about 12 g dry weight per liter culture volume, and 10 ml of the cells were added to 50 ml MS medium containing the vitamin mixture (Table I), 5 uM 2,4-D,±5 uM BA and 30 g/l sucrose in a 125 ml Erlenmeyer flask. The resin (5 g of XAD-4 resin) was added to the flask. The resin was washed with methanol and dried under vacuum prior to use. The flask was incubated for 6 days at 26° C. in the dark at an agitation speed of 150 rpm. The flask contents were harvested and analyzed for vanillin and other vanilla flavor components as described in Example 12. About 55 mcg of flavor material was detected in 60 ml of culture. In contrast, flasks without XAD-4 resin supplement produced nine-fold lower amounts of flavor material.

EXAMPLE 7

Producing Vanilla Flavor Composition

The cultured cells of *V. fragrans* from Example 5 were grown with a hormone supplement of 5 uM 2,4-D and 5 uM BA to a cell density of about 12 g per liter and 10 ml of the cells were added to a 125 ml Erlenmeyer flask containing 50 ml MS medium, vitamin mixture (Table I) and 30 g/l lactose. Washed XAD-4 resin (5 g) was added to the culture. The flask was incubated for 29 days at 26° C. in the dark at an agitation speed of 150 rpm. On day 29, 5 ml of the culture resin mixture was withdrawn for analysis and replaced with 5 g of washed XAD-4 resin. On day 38, a second sample was taken and 5 more g of XAD-4 resin was added. The final sample was taken at day 47 when the culture was terminated. Analysis for vanillin and vanilla flavor components was performed as described in Example 12. About 900 mcg of flavor material was detected in 50 ml of culture medium. Results were as follows:

| Time (days) | Vanillin (mg/l) |
| --- | --- |
| 29 | 1.8 |
| 38 | 9.7 |
| 47 | 18.0 |

EXAMPLE 8

The cultured suspensions of *V. fragrans* from Example 5 were grown with a hormone supplement of 20 uM 2,4-D and 5 uM kinetin to cell densities of 12 g/l over a 7–8 period at 28° C. in 500 ml Erlenmeyer flasks with 200 ml medium at a shaker speed of 150 rpm. Contents of 4 such flasks were mixed thoroughly in a 1 liter Erlenmeyer flask. 70 ml of this culture was added to 90 ml medium in a 500 ml flask. 10 such flasks were prepared. Activated charcoal powder (Sigma Chemical Co., St. Louis, Mo.) was added to each set of duplicate flasks at concentrations of 1 g/l, 3 g/l, 10 g/l and 40 g/l respectively. Duplicate flasks without charcoal were used as controls. The flasks were shaken at 150 rpm at a temperature of 26° C. Flask contents were harvested after 6 days and analyzed for vanillin and other vanilla flavor components as described below. Table 3 details vanillin production by the cultures over a 6 day period at various levels of charcoal.

TABLE 3

Vanillin Accumulation in *V.fragrans* cell suspensions at various charcoal concentrations

| Charcoal Concentration (g/L) | Vanillin Production (mg/L) |
| --- | --- |
| 0 | 0.3 ± 0.1 |
| 1 | 1.35 ± 0.15 |
| 3 | 1.8 ± 0.1 |
| 10 | 7.3 ± 0.6 |
| 40 | 16.3 + 0.8 |

The analytical procedure for extraction and quantitation of vanillin and other vanilla flavor components from cell suspensions mixed with activated charcoal was as follows: 5 ml of suspensions culture sample containing suspended vanilla cells, activated charcoal and nutrient media was centrifuged at 1000×g for 5 minutes. The liquid was discarded and the solid were extracted three times with 2 ml portions of 4/1 mixture of methanol and 1N KOH. Following removal of methanol, the extract was titrated to pH 2 with in HCl. The acidified extract was then extracted three times with 3 ml portions of methylbutyl ether. Methyl-butyl ether was back extracted with 400 ul 0.5N NaOH. This aqueous layer, after acidification, was analyzed by high performance liquid chromatography.

EXAMPLE 9

Cultured suspensions of *V. fragrans* as described in Example 8 were used to inoculate 4 reactor vessels of 1 liter capacity. The reactor vessel was fabricated from an inverted 2 liter Erlenmeyer flask and jacketed for temperature control. An air tube, 2 mm in I.D., was used to pump sterile air to each vessel. 450 ml suspensions (7–8 day old, stationary phase, approximate density=12 g/L) were added to 750 ml medium in each reactor vessel so that the initial cell density of 4.5 g/l (dry wt. basis) was obtained. Activated charcoal powder was then added to each vessel at amounts indicated below:

Reactor I—Complete medium with 10 g/L charcoal
Reactor II—Complete medium with 40 g/L charcoal
Reactor III—Minimal medium with 10 g/L charcoal
Reactor IV—Minimal medium with 40 g/L charcoal The cultures were aerated with sterile and humidified ambient air at flow rates of 0.5 volume air/volume culture/min. 5 ml samples were aseptically withdrawn from each reactor vessel on days 0, 3, 6, 9, 11, 14 and 19, and analyzed for their content of vanillin and other vanilla flavor components as per procedure described in Example 9. The results are plotted in FIG. 4. Thus over a 19 day cultivation period, highest levels of vanillin produced in reactors I–IV were 14 mg/L, 45 mg/L, 21 mg/L and 99 mg/L respectively. Thus, the use of minimal medium led to a 50% to 120% higher level of vanillin accumulation as compared to the complete medium.

The compositions of the complete medium and the minimal medium were as follows:

| Complete Medium | Minimal Medium |
| --- | --- |
| MS salts | 0.51 g/L CaCl$_2$ 2H$_2$O |
| Vitamins from Table 1 | 2.9 g/L NaCl |
| 20 um 2,4-D | 30 g/L sucrose |
| 5 um kinetin | pH = 5.8 |
| 30 g/L sucrose | |
| pH = 5.8 | |

Example 10

Flavor Production and Leakage by Immobilized Vanilla Cells

Cultured suspensions of *V. fragrans* as described in Examples 8 and 9 were grown to a cell density of 11–12 g/L in 7 days. 25 ml of the cell suspension was concentrated roughly 2-fold by centrifugation. 15 ml of the concentrated suspension was mixed with 20 ml of 2.4% sodium alginate solution and pipetted dropwise into 100 ml of 2% w/v calcium chloride solution. Formation of calcium alginate beads (containing vanilla cells) ensued; these beads were cured for 2 hours in the calcium chloride solution. Beads were washed twice in phosphate deficient MS medium.

The beads were suspended in 50 ml of D/K=20/5 medium deficient of phosphate and containing 500 mg of powdered charcoal in a 125 ml flask, and shaken at 150 rpm at 28° C. for a period of 8 days. 2 ml samples of the medium-activated charcoal mix were withdrawn aseptically and analyzed for vanillin and other vanilla flavor components as per procedure described in Example 8.

| Cultivation Time (days) | Vanillin Amount in media/flask (ug/flask) |
| --- | --- |
| 0 | 0 |
| 1 | 70 |
| 3 | 165 |
| 7 | 360 |
| 8 | 435 |

EXAMPLE 11

Flavor Production in a Reactor System

The cultured callus cells from Example 5 were grown as described in Example 8. Approximately 75 ml of the 7 day cell suspension with an approximate density of 7–8% were mixed with 35 ml of 2.4% sodium alginate solution and pipetted dropwise into 250 ml of 3% w/v calcium chloride solution. Formation of calcium alginate beads (containing cells) ensued; these beads were cured in 3% w/v calcium chloride solution for 2 hours. Beads were washed twice in (phosphate deficient) MS medium.

The beads were packed into a 2.5 cm diameter reactor to a final height of 8 cm. Aerated medium, containing 3% sucrose, vitamin mix, minus potassium phosphate was circulated through the reactor bed at a flow rate of 100 ml/min. Circulation loop included one column containing 13 grams of XAD-4 resin.

At the end of day 5, circulation was diverted from the first XAD-4 column to a second, identical column containing XAD-4 resin. Circulation was continued for 8 days.

Analysis for vanillin and vanilla flavor components was performed as described in Example 7. Results were as follows:

|  | Column 1 (mcg) | Column 2 (mcg) |
|---|---|---|
| 1. Vanillin | 52 | 41 |
| 2. Vanillyl alcohol | 2.8 | 13 (total for 2–5) |
| 3. 4-hydroxybenzaldehyde | 2.5 | |
| 4. 4-hydroxybenzoic acid | 4.9 | |
| 5. Vanillic acid | 6.0 | |

EXAMPLE 12

HPLC Characterization of Vanilla Flavors

HPLC analysis of the vanilla flavor material obtained in Example 7 was performed by HPLC, using a 4.6 mm id×15 cm HPLC column packed with octadecylsilyl reverse-phase packing material. The extracted vanilla material was dissolved in 505 methanol, final concentration 10 mg/ml, and 10 lambda of the solution was applied to the column. The material was eluted with a linear gradient from 5% methanol to 25% methanol containing 0.5% acetic acid. The column peaks were monitored at 280 nm.

The chromatogram is shown in FIG. 3B. For comparison, a chromatogram obtained by identical HPLC analysis of commercial vanilla bean extract, diluted 1:20, is shown in FIG. 3A. The peak identities, as determined by spectral character and external standards are shown in the figure.

As seen, the vanilla flavor extract contains a high percentage of vanillin, relatively low amounts of the compounds associated with peaks 1–4, and relatively large amounts of slower eluting material.

Although the invention has been described with respect to particular methods and products, it will be apparent that various changes and modifications may be made without departing from the invention.

APPENDIX—Reference Citations

Al-Abta, S., et al, Plant Sci. Lett. 16, 129–134.
Berker, H., Biochem Physiol Pflanz 161:425 (1970).
Collin, H. A., et al in *Handbook of Plant Cell Culture*, Vol 1 (D. Evans et al, eds) Macmillan, pp. 729–747 (1983).
Dodds, J. H., et al, in *Plant Tissue Culture*, Cambridge Univ Press, pp. 54–69 and pp. 180–188 (1986).
Dougall, D. K., in *Adv in Experimental Med and Biol* (J. Petreciana et al, eds.) Plenum Press, pp. 136–151 (1980).
Jalal, M. A. F., et al, New Phytol 83:343 (1979).
Sarkar, K. S., et al, J Agric Food Chem 24(2):317 (1976).
Selby, C., et al, New Phytol 84:307 (1980).
Staba, E. J., Dev Microbiol 4 193 (1963).
Turnbull, A., et al, New Phytol 87:257 (1981).
Weiler, E. W., in *Plant Tissue Culture and its Bio-Technical Application* (W. Barz et al, eds) Springer-Verlag, pp. 266–277 (1977).
Widholm, J. M., in *Plant Tissue Culture and its Biotechnical Applications* (W. Barz et al, eds) Springer Verlag, pp. 112–122 (1977).
Yeoman, M. M., et al in *Differentiation In Vitro, 4th Symposium Brit Soc Cell Biol*, Cambridge Univ Press, pp. 65–81 (1981).
Zenk, M. H., in *Frontiers of Plant Tissue Culture* (T. Thorpe, ed.), Calgary Univ Press, Calgary p. 1–13 (1978).

It is claimed:

1. A vanilla flavor composition useful for imparting a vanilla flavor to a foodstuff comprising:
   a) vanilla cell culture extract containing vanillin; and
      i) a first set of vanilla flavor components which elute before vanillin on an HPLC column eluted with methanol/acetic acid gradient; and
      ii) a second set of vanilla flavor components which elute after vanillin on an HPLC column eluted with methanol/acetic acid gradient;
   b) said extract has a ratio of vanillin to the combined amounts of said first set of vanilla flavor components which is substantially greater than is present in a natural vanilla extract of vanilla beans; and
   c) said extract has a ratio of vanillin to the combined amounts of said second set of vanilla flavor components which is substantially less than is present in a natural vanilla extract of vanilla beans.

2. A cultured vanilla flavor extract as in claim 1 which includes:
   a) a high percentage of vanillin;
   b) a low amount of said first set of flavor components; and
   c) a large amount of said second set of flavor components.

3. A cultured vanilla flavor extract composition as in claim 2 wherein:
   a) said first set of flavor components includes at least one of vanillic acid, 3,4-dihydroxybenzaldehyde, 4-hydroxybenzoic acid and 4-hydroxybenzaldehyde, the alcohol derivatives of said acids, and combinations thereof.

4. A cultured vanilla flavor extract composition as in claim 3 wherein:
   a) said HPLC elution chromatogram exhibits a predominant vanillin peak.

5. A cultured vanilla flavor extract composition as in claim 4 wherein:
   a) said HPLC chromatogram exhibits the peaks of FIG. 3b.

6. A cultured vanilla flavor extract composition as in claim 1 in which:
   a) said extract is selected from the group consisting essentially of an aqueous solution, an ethanolic solution, mixtures thereof, and evaporites thereof.

7. A cultured vanilla flavor extract composition as in claim 6 wherein:
   a) said extract is derived from a suspension of undifferentiated vanilla plant species callus cells cultured with a minimal medium.

8. A cultured vanilla flavor extract composition as in claim 7 wherein:
   a) said vanilla plant species callus cell culture is selected from the group consisting of callus cells of *V. fragrans, V. phaeantha, V. pompena, V. tahitensis* and combinations thereof.

9. A cultured vanilla flavor extract composition as in claim 8 wherein:
   a) said vanilla plant species callus cell culture is selected from the group consisting of callus cells of *V. fragrans, V. phaeantha* and combinations thereof.

10. A cultured vanilla flavor extract composition as in claim 4 in which:
    a) said extract is selected from the group consisting essentially of an aqueous solution, an ethanolic solution, mixtures thereof, and evaporites thereof.

11. A cultured vanilla flavor extract composition as in claim 10 wherein:
   a) said extract is derived from a suspension of undifferentiated vanilla plant species callus cells cultured with a minimal medium.

12. A cultured vanilla flavor extract composition as in claim 11 wherein:
   a) said vanilla plant species callus cell culture is selected from the group consisting of callus cells of *V. fragrans, V. phaeantha, V. pompena, V. tahitensis* and combinations thereof.

13. A cultured vanilla flavor extract composition as in claim 12 wherein:
   a) said vanilla plant species callus cell culture is selected from the group consisting of callus cells of *V. fragrans, V. phaeantha* and combinations thereof.

14. A cultured vanilla-flavored food comprising:
   a) a processed food; and
   b) a vanilla cell culture extract as in claim 1 present in said food in an amount sufficient to provide a distinctive cultured vanilla flavor thereto.

15. A cultured vanilla-flavored food as in claim 14 wherein:
   a) said vanilla cell culture extract is an extract as in claim 4.

16. A cultured vanilla-flavored food as in claim 14 wherein:
   a) said vanilla cell culture extract is an extract as in claim 7.

17. A cultured vanilla-flavored food as in claim 14 wherein:
   a) said vanilla cell culture extract is an extract as in claim 8.

* * * * *